United States Patent
Kusaka et al.

(10) Patent No.: US 11,806,414 B2
(45) Date of Patent: *Nov. 7, 2023

(54) SILICA-INCLUDING MICROCAPSULE RESIN PARTICLES, METHOD FOR PRODUCING SAME, AND APPLICATION THEREOF

(71) Applicant: SEKISUI PLASTICS CO., LTD., Osaka (JP)

(72) Inventors: Akiyoshi Kusaka, Nara (JP); Yoshinao Yamaji, Nara (JP); Ryosuke Harada, Shiga (JP)

(73) Assignee: SEKISUI PLASTICS CO., LTD., Osaka (JP)

( * ) Notice: Subject to any disclaimer, the term of this patent is extended or adjusted under 35 U.S.C. 154(b) by 263 days.

This patent is subject to a terminal disclaimer.

(21) Appl. No.: 17/173,334

(22) Filed: Feb. 11, 2021

(65) Prior Publication Data

US 2021/0161776 A1 Jun. 3, 2021

Related U.S. Application Data

(63) Continuation of application No. 16/070,675, filed as application No. PCT/JP2017/007390 on Feb. 27, 2017, now Pat. No. 10,952,938.

(30) Foreign Application Priority Data

Feb. 29, 2016 (JP) ................. 2016-037351

(51) Int. Cl.
| | |
|---|---|
| *A61K 9/50* | (2006.01) |
| *A61K 8/11* | (2006.01) |
| *A61K 8/25* | (2006.01) |
| *A61Q 19/00* | (2006.01) |
| *A61K 8/02* | (2006.01) |
| *C01B 33/159* | (2006.01) |
| *G02B 1/04* | (2006.01) |
| *B32B 27/18* | (2006.01) |
| *C09D 7/40* | (2018.01) |
| *A61Q 1/00* | (2006.01) |
| *G02B 5/02* | (2006.01) |
| *B01J 13/06* | (2006.01) |
| *C09D 7/65* | (2018.01) |
| *C09D 7/61* | (2018.01) |
| *A61Q 1/12* | (2006.01) |
| *B01J 13/18* | (2006.01) |

(52) U.S. Cl.
CPC ............... *A61K 8/11* (2013.01); *A61K 8/02* (2013.01); *A61K 8/0279* (2013.01); *A61K 8/25* (2013.01); *A61Q 1/00* (2013.01); *A61Q 1/12* (2013.01); *A61Q 19/00* (2013.01); *B01J 13/06* (2013.01); *B01J 13/185* (2013.01); *B32B 27/18* (2013.01); *C01B 33/159* (2013.01); *C09D 7/40* (2018.01); *C09D 7/61* (2018.01); *C09D 7/65* (2018.01); *C09D 7/68* (2018.01); *C09D 7/69* (2018.01); *G02B 1/04* (2013.01); *G02B 5/02* (2013.01); *G02B 5/0226* (2013.01); *A61K 2800/10* (2013.01); *A61K 2800/412* (2013.01); *A61K 2800/614* (2013.01); *A61K 2800/651* (2013.01); *A61K 2800/654* (2013.01)

(58) Field of Classification Search
None
See application file for complete search history.

(56) References Cited

U.S. PATENT DOCUMENTS

| | | | | |
|---|---|---|---|---|
| 4,972,000 | A * | 11/1990 | Kawashima | ............ C08F 2/16 427/222 |
| 2004/0253443 | A1 | 12/2004 | Anselmann et al. | |
| 2009/0053524 | A1 | 2/2009 | Yamada et al. | |
| 2010/0028700 | A1* | 2/2010 | Wu | ....................... G03G 15/162 428/474.4 |
| 2014/0106032 | A1 | 4/2014 | Dardelle et al. | |

FOREIGN PATENT DOCUMENTS

| | | |
|---|---|---|
| JP | 2005-82746 | 3/2005 |
| JP | 2009-209209 | 9/2009 |
| JP | 2009-237342 | 10/2009 |
| JP | 2011-225381 | 11/2011 |
| JP | 2012-167286 | 9/2012 |
| JP | 2014-523336 | 9/2014 |
| TW | I262194 | 9/2006 |
| TW | 200722782 | 6/2007 |
| WO | 2007/037202 | 4/2007 |
| WO | 2014/030754 | 2/2014 |

OTHER PUBLICATIONS

Suzuki et al., "Preparation of Silica-Including Microcapsules by Sol-Gel Reaction in Polymer Capsules", Polymer Preprints, Japan vol. 64, No. 2, 1R11, (2015).

ISR issued in International Patent Application No. PCT/JP2017/007390, dated May 30, 2017, English translation.

* cited by examiner

*Primary Examiner* — Susan T Tran

(74) *Attorney, Agent, or Firm* — GREENBLUM & BERNSTEIN, P.L.C.

(57) ABSTRACT

Silica-including microcapsule resin particles including an outer shell constituted of a crosslinked polymer and a cavity partitioned with the outer shell, in which the silica-including microcapsule resin particles contain inside the cavity a porous structure in which silica particles are mutually connected, and have a volume average particle diameter of 0.5 to 100 μm.

14 Claims, 3 Drawing Sheets

(a) (b)

(a) (b)

(a) (b)

(a) (b)

(a) (b)

(a) (b)

(a)       (b)

(a)       (b)

SILICA-INCLUDING MICROCAPSULE RESIN PARTICLES, METHOD FOR PRODUCING SAME, AND APPLICATION THEREOF

CROSS-REFERENCE TO RELATED APPLICATIONS

The present application is a continuation application of U.S. patent application Ser. No. 16/070,675, which is a National Phase application of International Application No. PCT/JP2017/007390, filed on Feb. 27, 2017, and claims the benefit of Japanese Patent Application No. 2016-037351, filed on Feb. 29, 2016. The entire disclosure of each of the above-identified applications, including the specification, drawings, and claims, is incorporated herein by reference in its entirety.

TECHNICAL FIELD

The present invention relates to silica-including microcapsule resin particles, method for producing same, and application thereof (silica-including microcapsule resin particles, a method for producing the same, and use of the same). More particularly, the present invention relates to silica-including microcapsule resin particles having a peculiar shape, a method for producing the same, and use of the same. The silica-including microcapsule resin particles of the present invention are suitable for intended use such as cosmetic materials, paint compositions, heat-insulating resin compositions, light diffusing resin compositions, and light diffusion films, which utilize properties thereof.

BACKGROUND TECHNOLOGY

Conventionally, in intended use such as cosmetic materials, paint compositions, heat-insulating resin compositions, light diffusing resin compositions, and light diffusion films, resin particles, silica particles, glass particles, and inorganic fine particles of titanium oxide, alumina, calcium carbonate or the like are used as an additive, for improving the sense of touch, imparting the soft focus effect, matting property, and light diffusibility, or the like.

As a specific additive, for example, hollow resin particles (Japanese Unexamined Patent Application, First Publication No. 2009-237342: Patent Document 1; International Publication WO 2014/030754: Patent Document 2) have been proposed.

Additionally, a method of obtaining microcapsule particles including a single or a plurality of silica particle(s) by applying a method of synthesizing hollow particles having a micron size to prepare microcapsule particles including a silica precursor, and thereafter, performing a sol-gel reaction has been proposed (Polymer Preprint, Japan Vol. 64, No. 2 (2015) 1R11 (Preparation of Silica-Including Microcapsules by Sol-Gel Reaction in Polymer Capsules, Suzuki et al.): Non-Patent Document 1).

PRIOR ART DOCUMENTS

Patent Documents

Patent Document 1: Japanese Unexamined Patent Application, First Publication No. 2009-237342
Patent Document 2: International Publication WO 2014/030754

Non-Patent Documents

Non-Patent Document 1: (Polymer Preprint, Japan Vol. 64, No. 2 (2015) 1R11 (Preparation of Silica-Including Microcapsules by Sol-Gel Reaction in Polymer Capsules, Suzuki et al.)

SUMMARY OF THE INVENTION

Problem to be Solved by the Invention

However, it is impossible to state that hollow resin particles of Patent Documents 1 and 2 and microcapsule particles including a single or a plurality of silica particle(s) of Non-Patent Document 1 have, for example, sufficient light scattering property due to the inner space, and have been insufficient for obtaining high light diffusing property and opacifying property. For that reason, provision of resin particles having high light diffusing property has been demanded.

Means for Solving the Problem

The inventors of the present invention have found out that silica-including microcapsule resin particles, in which an outer shell is constituted of a crosslinked polymer, and the particles contain silica having a porous structure inside the capsules can solve the above-mentioned problem, arriving at the present invention.

Thus, according to the present invention, there is provided silica-including microcapsule resin particles, comprising an outer shell constituted of a crosslinked polymer and a cavity partitioned with the outer shell, wherein the silica-including microcapsule resin particles contain inside the cavity a porous structure in which silica particles are mutually connected, and have a volume average particle diameter of 0.5 to 100 μm.

Also, according to the present invention, there is provided a method for producing the silica-including microcapsule resin particles, the method comprising the steps of; suspension polymerizing a mixture containing 100 parts by weight of a radical polymerizable monofunctional monomer, 20 to 80 parts by weight of a crosslinking monomer, and 60 to 200 parts by weight of silicone alkoxide as a silica precursor in presence of a radical polymerization initiator in an aqueous medium to form an outer shell constituted of a crosslinked polymer and a cavity partitioned with said outer shell; and gelling silicone alkoxide after formation of said outer shell or together with formation of said outer shell to form inside said cavity a porous structure in which silica particles are mutually connected.

Furthermore, according to the present invention, there is provided a cosmetic material comprising the silica-including microcapsule resin particles.

Also, according to the present invention, there is provided a paint composition comprising the silica-including microcapsule resin particles.

Furthermore, according to the present invention, there is provided a heat-insulating resin composition comprising the silica-including microcapsule resin particles.

Also, according to the present invention, there is provided a light diffusing resin composition comprising the silica-including microcapsule resin particles.

Furthermore, according to the present invention, there is provided a light diffusion film comprising the silica-including microcapsule resin particles.

Effects of Invention

According to the present invention, there can be provided silica-including microcapsule resin particles which exert the remarkable effect of excellent light diffusibility and opacifying property.

Also, in any of the following cases, there can be provided silica-including microcapsule resin particles which exert the remarkable effect of more excellent light diffusibility and opacifying property.

(1) The porous structure has a weight that is 5 to 50% of a total weight of the silica-including microcapsule resin particles and gives a hollow structure to the cavity.

(2) The outer shell is porous.

(3) The outer shell is porous, and the silica-including microcapsule resin particles have an oil absorption of 150 to 500 ml/100 g.

(4) The outer shell is non-porous, and the silica-including microcapsule resin particles have an apparent specific density of 0.3 to 1.0 g/cm$^3$.

Furthermore, in any of the following cases, there can be provided a method by which the above-mentioned silica-including microcapsule resin particles can be produced more simply.

(a) The silicone alkoxide is a mixture including a monomer and an oligomer.

(b) The suspension polymerization is performed in absence of a non-reactive organic solvent and in presence of an alkoxide compound of titanium, zirconium or aluminum.

(c) The gellation is performed with a catalyst of an acid or a base in the cavity partitioned with the outer shell, the acid or the base is generated by external stimulation of energy radiation or heat to a latent pH adjusting agent, and the latent pH adjusting agent exists in the cavity by dissolving the latent pH adjusting agent in the mixture during the suspension polymerization.

Figure 1:
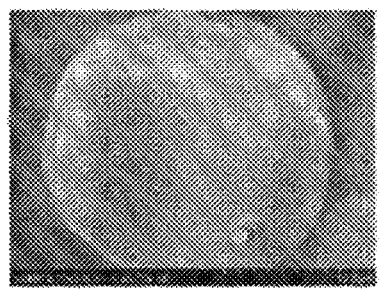
FIG. 1 is a surface photograph and a cross-sectional photograph of silica-including microcapsule resin particles of Example 1.
Figure 1:
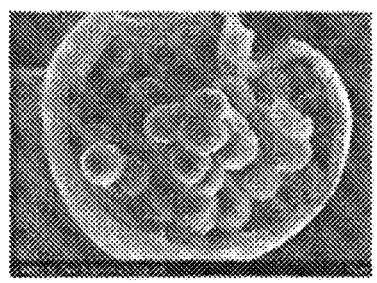

BEST MODE FOR CARRYING OUT THE INVENTION (Silica-Including Microcapsule Resin Particles)

Silica-including microcapsule resin particles (hereinafter, also referred to as silica-including particles) comprise an outer shell constituted of a crosslinked polymer and a cavity partitioned with the outer shell. Additionally, silica-including particles comprise, inside the cavity, a porous structure in which silica particles are mutually connected. Furthermore, silica-including particles have a volume average particle diameter of 0.5 to 100 μm.

(1) Outer Shell

A kind of the crosslinked polymer is not particularly limited, as far as the crosslinked polymer can constitute the outer shell. Examples of the crosslinked polymer include a polymer derived from a radical polymerizable monomer, and specifically, examples include a copolymer of a monofunctional monomer having one vinyl group and a crosslinking monomer having two or more vinyl groups.

Examples of the monofunctional monomer having one vinyl group include alkyl (meth)acrylates having 1 to 8 carbon atoms such as methyl (meth)acrylate, ethyl (meth) acrylate, butyl (meth)acrylate, and cetyl (meth)acrylate; (meth)acrylonitrile, dimethyl maleate, dimethyl fumarate, diethyl fumarate, ethyl fumarate, maleic anhydride, N-vinylcarbazole; styrene-based monomers such as styrene, α-methylstyrene, paramethylstyrene, vinyltoluene, chlorostyrene, ethylstyrene, i-propylstyrene, dimethylstyrene, bromostyrene; and the like. These monofunctional monomers can be used alone or can be used by combining a plurality of them.

Examples of the crosslinking monomer having two or more vinyl groups include polyfunctional acrylic esters such as ethylene glycol di(meth)acrylate, polyethylene glycol di(meth)acrylate, and glycerin tri(meth)acrylate; polyfunctional acrylamide derivatives such as N,N'-methylenebis(meth)acrylamide and N,N'-ethylenebis(meth)acrylamide; polyfunctional allyl derivatives such as diallylamine and tetraallyloxyethane; aromatic divinyl compounds such as divinylbenzene; and the like. These crosslinking monomers can be used alone or can be used by combining a plurality of them.

It is preferable that the crosslinking monomer is contained in the outer shell at the ratio of 10 parts by weight or more based on 100 parts by weight of the whole radical monomer. When the content of the crosslinking monomer is less than 10 parts by weight, the outer shell having the sufficient strength may not be formed. When the content is more than 80 parts by weight, the outer shell may become porous, and depending on the intended use, permeation of a binder resin or the like into the interior of silica-including particles may not be suppressed. When one tries to obtain a non-porous outer shell, it is more preferable that the content is 20 to 70 parts by weight and more preferably 30 to 55 parts by weight. When one tries to obtain a porous outer shell, it is preferable that the content is more than 80 parts by weight.

(2) Porous Structure Composed of Silica

The porous structure has a configuration in which silica particles are mutually connected. Herein, the porous structure means a structure in which a part of a plurality of silica particles is mutually connected, and at an unconnected part, gaps as a macropore are formed between silica particles. It is preferable that the porous structure has a volume at a range of the ratio based on the whole volume of the cavity, described in the following column of various physical properties.

Furthermore, individual silica particles are mainly composed of $SiO_2$. Silica particles can be obtained, for example, by gelling a silica precursor. Examples of the silica precursor include silicone alkoxides having one or more silicon atoms and an alkoxy group (for example, carbon number 1 to 4) in the same molecule. Specifically, examples thereof include tetraethoxysilane (TEOS), tetramethoxysilane, tetrapropoxysilane, and the like. Additionally, examples include oligomers such as a methyl silicate oligomer which is a partially hydrolyzed oligomer of tetramethoxysilane (manufactured by Mitsubishi Chemical Corporation, product name: MKC Silicate), an ethyl silicate oligomer which is a partially hydrolyzed oligomer of tetraethoxysilane (manufactured by Tama Chemicals Co., Ltd., product name: Silicate 45 (pentamer), Silicate 48 (decamer)), and a siloxane oligomer. These silica precursors can be used alone or can be used by combining a plurality of them. Among them, as a monofunctional silica precursor, tetraethoxysilane is preferable, and as the silica precursor which is an oligomer, an ethyl silicate siloxane oligomer is preferable.

It is preferable that the porous structure exists on an inner wall of the outer shell, in order to impart excellent light diffusibility and opacifying property to silica-including particles.

(3) Various Physical Properties (a) Volume Average Particle Diameter

Silica-including particles have a volume average particle diameter of 0.5 to 100 µm. When the volume average particle diameter is less than 0.5 µm, it is difficult to obtain fine capsule particles. When the volume average particle diameter is more than 100 µm, it is difficult to produce silica-including particles due to collapse of capsule particles. The volume average particle diameter can take 0.5 µm, 1 µm, 10 µm, 20 µm, 30 µm, 40 µm, 50 µm, 70 µm, 90 µm, and 100 µm. Depending on intended use, the volume average particle diameter is preferably 3 to 80 µm, and more preferably 5 to 50 µm.

(b) Apparent Specific Gravity

When the outer shell is non-porous, it is preferable that silica-including particles have an apparent specific gravity of 0.3 to 1.0 $g/cm^3$. When the apparent specific gravity is less than 0.3 $g/cm^3$, a resin layer of the outer shell may be thin and the strength may be reduced. When the apparent specific gravity is more than 1.0 $g/cm^3$, the effect due to the porous structure composed of silica in the interior may not be sufficiently exerted. The apparent specific gravity can take 0.3 $g/cm^3$, 0.4 $g/cm^3$, 0.5 $g/cm^3$, 0.6 $g/cm^3$, 0.7 $g/cm^3$, 0.8 $g/cm^3$, 0.9 $g/cm^3$, and 1.0 $g/cm^3$. The apparent specific gravity is preferably 0.3 to 0.9 $g/cm^3$.

(c) External Shape and the Like

An external shape of silica-including particles is not particularly limited, but is preferably near to a spherical shape as much as possible.

A thickness of the outer shell is preferably 5 to 40% of a volume average particle diameter. When the thickness is less than 5%, the outer shell may not have the sufficient strength. When the thickness is more than 40%, the effect due to the internal silica structure may become insufficient. The thickness can take 5%, 10%, 15%, 20%, 25%, 30%, 35%, and 40%. The thickness is more preferably 10 to 30%.

The outer shell may be porous. By being porous, improvement in the strength of particles themselves can be expected as compared with general silica porous resin particles and hardly disintegrated particles can be provided. Additionally, it is also possible to improve the gap rate. Additionally, there is a problem that general porous resin particles are made to be porous employing a large amount of a pore making agent (solvent), and in order to obtain fine particles having great oil absorption, it is necessary to use a large amount of the pore making agent, and productivity is remarkably reduced, and so on. In contrast, in the particles of the present invention, the gap rate can exceed 90% in the porous structure composed of silica inside microcapsules, without using a large amount of the pore making agent. The porosity can be defined by oil absorption. Oil absorption is preferably 150 to 500 ml/100 g. Oil absorption can take 150 ml/100 g, 200 ml/100 g, 250 ml/100 g, 300 ml/100 g, 350 ml/100 g, 400 ml/100 g, 450 ml/100 g, and 500 ml/100 g. It is also possible to define the porosity by other indices such as a pore diameter and a pore volume.

It is preferable that the porous structure composed of silica has a weight that is 5 to 50% of the total weight of silica-including microcapsule resin particles. When the weight of the porous structure is less than 5%, formation of a porous body by silica may become insufficient. When the weight is more than 50%, the ratio of the outer shell may be relatively reduced and the outer shell may not have the sufficient strength. The weight can take 5%, 10%, 20%, 30%, 40%, 45%, and 50% of the total weight. The weight is preferably 10 to 45%.

(Method for Producing Silica-Including Particles)

A method for producing silica-including particles comprises a polymerization step of polymerizing a monomer in a mixture comprising a silica precursor and a radical polymerizable monomer, which has been emulsified and dispersed in an aqueous medium, to obtain microcapsules comprising the silica precursor in the interior thereof, and a gelling step of gelling the silica precursor in microcapsules, thereby, forming silica particles.

(1) Polymerization Step

In the polymerization step, first, a mixture comprising the silica precursor and the monomer is dispersed in an aqueous medium by emulsification. In addition, the use amount of the monomer and the content of monomer-derived components constituting the outer shell are substantially consistent.

Emulsification dispersion is not particularly limited, but emulsification dispersion is performed while appropriately adjusting various conditions such as a stirring speed and a stirring time, so that silica-including particles having a desired particle diameter are obtained.

It is preferable that polymerization of the monomer is performed in the presence of a polymerization initiator. The polymerization initiator is not particular limited, but examples thereof include persulfuric acid salts such as ammonium persulfate, potassium persulfate, and sodium persulfate; organic peroxides such as cumene hydroperoxide, di-tert-butyl peroxide, dicumyl peroxide, benzoyl peroxide, lauroyl peroxide, dimethylbis(tert-butylperoxy) hexane, dimethylbis(tert-butylperoxy)hexyne-3, bis(tert-butylperoxyisopropyl)benzene, bis(tert-butylperoxy) trimethylcyclohexane, butyl-bis(tert-butylperoxy)valerate, 2-ethylhexaneperoxoic acid tert-butyl, dibenzoyl peroxide, paramenthane hydroperoxide, and tert-butyl peroxybenzoate; and azo compounds such as 2,2'-azobis[2-(2-imidazolin-2-yl) propane]dihydrochloride, 2,2'-azobis[2-(2-imidazolin-2-yl)propane]disulfate dihydrate, 2,2'-azobis(2-amidinopropane)dihydrochloride, 2,2'-azobis[N-(2-carboxyethyl)-2-methylpropionamidine]hydrate, 2,2'-azobis{2-[1-(2-hydroxyethyl)-2-imidazolin-2-yl] propane}dihydrochloride, 2,2'-azobis[2-(2-imidazolin-2-yl) propane], 2,2'-azobis(1-imino-1-pyrrolidino-2-ethylpropane)dihydrochloride, 2,2'-azobis{2-methyl-N-[1,1-bis(hydroxymethyl)-2-hydroxyethyl]propanamide}, 2,2'-azobis[2-methyl-N-(2-hydroxyethyl)propionamide], 4,4'- azobis(4-cyanopentanoic acid), 2,2'-azobisisobutyronitrile, 2,2'-azobis(2-methyl-butyronitrile), 2,2'-azobis(2-isopropylbutyronitrile), 2,2'-azobis(2,3-dimethylbutyronitrile), 2,2'-azobis(2,4-dimethylbutyronitrile), 2,2'-azobis(2-methylcapronitrile), 2,2'-azobis(2,3,3-trimethylbutyronitrile), 2,2'-azobis(2,4,4-trimethylvaleronitrile), 2,2'-azobis(2,4-dimethylvaleronitrile), 2,2'-azobis(2, 4-dimethyl-4-ethoxyvaleronitrile), 2,2'-azobis(2,4-dimethyl-4-n-butoxyvaleronitrile), 2,2'-azobis(4-methoxy-2,4-dimethylvaleronitrile), 2,2'-azobis[N-(2-propenyl)-2-methylpropionamide], 2,2'-azobis(N-butyl-2-methylpropionamide), 2,2'-azobis(N-cyclohexyl-2-methylpropionamide), 1,1'-azobis(1-acetoxy-1-phenylethane), 1,1'-azobis(cyclohexane-1-carbonitrile), dimethyl-2,2'-azobis(2-methylpropionate), dimethyl-2,2'-azobisisobutyrate, dimethyl-2,2'-azobis(2-methylpropionate), 2-(carbamoylazo)isobutyronitrile, and 4,4'-azobis(4-cyanovaleric acid). These polymerization initiators can be used alone or can be used by combining a plurality of them.

It is preferable that the polymerization initiator is contained in the mixture at 0.05 to 5 parts by weight, based on 100 parts by weight of the monomer.

Examples of the aqueous medium include water, a mixture of water and a water-soluble organic solvent (for example, lower alcohol such as methanol and ethanol), and the like.

Additionally, the polymerization may be performed in the presence of a non-reactive organic solvent. Examples of the non-reactive organic solvent include butane, pentane, hexane, cyclohexane, heptane, decane, hexadecane, toluene, xylene, ethyl acetate, butyl acetate, methyl ethyl ketone, methyl isobutyl ketone, 1,4-dioxane, methyl chloride, methylene chloride, chloroform, carbon tetrachloride, and the like. These non-reactive organic solvents can be used alone or can be used by combining a plurality of them.

An addition amount of the non-reactive solvent is not particularly limited, but is 0 to 300 parts by weight, based on 100 parts by weight of the monomer. When the addition amount exceeds 300 parts by weight, formation of microcapsules may become insufficient.

In the present invention, in order to obtain silica-including microcapsules having a non-porous outer shell, the non-reactive organic solvent may be used in a range of 10 to 50 parts by weight, based on 100 parts by weight of the monomer. Depending on a kind of the solvent to be used, when an amount thereof exceeds 50 parts by weight, it becomes easy to obtain silica-including microcapsules having a porous outer shell.

Furthermore, by performing polymerization in the presence of an alkoxide compound of titanium, zirconium or aluminum, which has higher hydrolyzability as compared with silane alkoxide, a silica porous structure can be easily formed in capsules. When these alkoxide compounds are used, it is not necessary to use the non-reactive organic solvent. That is, the present inventors think that since these compounds have higher hydrolyzability than that of the silica precursor such as silane alkoxide, there is the effect that they are gelled in microcapsules and suppress migration of the silica precursor in capsules to promote the outer shell to become porous.

Examples of the alkoxide compound of titanium include isopropyltriisostearoyl titanate, isopropyltristearoyl titanate, isopropyltrioctanoyl titanate, isopropyldimethacrylisostearoyl titanate, isopropyltridodecylbenzenesulfonyl titanate, isopropylisostearoyldiacryl titanate, isopropyltri(dioctylphosphate)titanate, isopropyltricumylphenyl titanate, isopropyltris(dioctylpyrophosphate)titanate, isopropyltri(n-aminoethyl-aminoethyl)titanate, tetraisopropylbis(dioctylphosphite)titanate, tetraoctylbis(ditridecylphosphite)titanate, tetra(2,2-diallyloxymethyl-1-butyl)bis(ditridecyl)phosphite titanate, dicumylphenyloxyacetate titanate, bis(dioctylpyrophosphate)oxyacetate titanate, diisostearoylethylene titanate, bis(dioctylpyrophosphate)ethylene titanate, bis(dioctylpyrophosphate)diisopropyl titanate, tetramethyl orthotitanate, tetraethyl orthotitanate, tetrapropyl orthotitanate, tetraisopropyltetraethyl orthotitanate, tetrabutyl orthotitanate, butyl polytitanate, tetraisobutyl orthotitanate, 2-ethylhexyl titanate, stearyl titanate, a cresyl titanate monomer, a cresyl titanate polymer, diisopropoxy-bis-(2,4-pentadionate)titanium (IV), diisopropyl-bis-triethanolaminotitanate, octylene glycol titanate, titanium lactate, acetoacetic ester titanate, diisopropoxybis(acetylacetonato)titanium, di-n-butoxybis(triethanolaluminato)titanium, dihydroxybis(lactato)titanium, titanium-isopropoxyoctylene glycolate, a tetra-n-butoxytitanium polymer, a tri-n-butoxytitanium monostearate polymer, a butyl titanate dimer, titanium acetylacetonate, polytitanium titanium acetylacetonate, titanium octylene glycolate, titanium lactate ammonium salt, titanium lactate ethyl ester, titanium triethanolaminate, polyhydroxytitanium stearate, and the like.

Examples of the alkoxide compound of zirconium include zirconium butyrate, zirconium acetylacetonate, acetylacetone zirconium butyrate, zirconium lactate, stearic acid zirconium butyrate, tetra(triethanolamine)zirconate, tetraisopropyl zirconate, and the like.

Examples of the alkoxide compound of aluminum include acetoalkoxyaluminum diisopropionate, aluminum ethylacetoacetate diisopropylate, aluminum tris(ethylacetoacetate), aluminum alkylacetoacetate diisopropylate (carbon number of alkyl is 1 to 20), aluminum monoacetylacetonate bis(ethylacetoacetate), aluminum tris(acetylacetonate), and the like.

These alkoxide compounds can be used alone or can be used by combining a plurality of them.

An addition amount of the alkoxide compound is not particularly limited, but is 10 parts by weight or less, based on 100 parts by weight of the monomer. When the addition amount exceeds 10 parts by weight, since when a monomer mixture is suspended or emulsified in an aqueous medium, sufficient dispersion stability of liquid drops cannot be retained and particles may not be obtained.

In addition, herein, when the alkoxide compound of titanium, zirconium or aluminum which has higher hydrolyzability as compared with the non-reactive organic solvent or silane alkoxide is not added, a single or a plurality of spherical silica particle(s) is (are) generated inside microcapsules and resin particles having a porous structure composed of silica inside capsules, which is an object of the present invention, cannot be obtained.

Then, the emulsification-dispersed mixture becomes microcapsules comprising the silica precursor in the interior thereof, by subjecting the monomer therein to polymerization. Polymerization is not particularly limited, but is performed while appropriately adjusting various conditions such as a polymerization temperature and a polymerization time, depending on kinds of the monomer and the polymerization initiator contained in the mixture. For example, the polymerization temperature can be 30 to 80° C. and the polymerization time can be 1 to 20 hours.

(2) Gelling Step

In a gelling step, the silica precursor in microcapsules present in an emulsified liquid becomes silica particles by a gelling reaction, thereby, silica-including particles are obtained. It is preferable that the gelling reaction is performed while the emulsified liquid is maintained alkaline (for example, pH 7 or more, specifically pH 10 to 14). Maintenance of alkalinity can be performed by adding a base such as an aqueous ammonia solution, sodium hydroxide, and potassium hydroxide to the emulsified liquid. An addition amount of the base is preferably 1 to 10 equivalents, based on the silica precursor.

The gelling step is not particularly limited, but can be performed under conditions necessary for the silica precursor to be gelled to become silica particles (temperature, time, stirring speed, and the like for gelling). For example, a gelling temperature can be 30 to 80° C. and a gelling time can be 1 to 24 hours.

The gelling step may be performed in the coexistence of a latent pH adjusting agent. By making the latent pH adjusting agent coexist, it becomes possible to reduce an amount of the base to be added to the emulsified liquid. For example, when ammonia is used as the base, in the case where the latent pH adjusting agent coexists, gelling can be effectively performed even if an ammonia amount is reduced to 3 equivalents or less (for example, ammonia is not used; 0.01 to 3 equivalents). Ability to reduce the base exerts the effect that workability at the time of production can be improved. A use amount of the latent pH adjusting agent varies depending on a kind of this agent, the production condition, and the like, and for example, is preferably 0.01 to 10 parts by weight based on 100 parts by weight of the silica precursor. The use amount is more preferably 0.1 to 5 parts by weight.

The latent pH adjusting agent includes substances which generate an acid or a base, by external stimulation such as irradiation of energy radiation and heating. Examples of energy radiation include infrared rays, visible light, ultraviolet rays, and the like.

Specific examples of the latent pH adjusting agent will be described below.

(i) Examples of the latent pH adjusting agent which generates an acid by heating (heat acid generator) include an aryldiazonium salt, a sulfonium salt, a iodonium salt, an ammonium salt, a phosphonium salt, an oxonium salt, an iron-allene complex, an aromatic silanol-ammonium complex, diallyliodonium salt-dibenzyloxy copper, an imidazole derivative, a benzylsulfonium salt, hemiacetal ester, sulfonic acid ester, and the like.

Additionally, examples thereof include dicyandiamide, cyclohexyl p-toluenesulfonate, diphenyl(methyl)sulfonium tetrafluoroborate, 4-hydroxyphenylbenzylmethylsulfonium tetrakis(pentafluorophenyl)borate, (4-acetoxyphenyl)benzylmethylsulfonium tetrakis(pentafluorophenyl)borate, 4-hydroxyphenylbenzylmethylsulfonium hexafluoroantimonate, 4-acetoxyphenylbenzylmethylsulfonium hexafluoroantimonate, triphenylsulfonium hexafluoroantimonate, triphenylsulfonium hexafluorophosphonate, di-tert-butylphenyliodonium hexafluorophosphonate, triarylsulfonium hexafluorophosphonate, bis(4-tert-butylphenyl)iodonium hexafluorophosphate, bis(4-fluorophenyl)iodonium trifluoromethanesulfonate, cyclopropyldiphenylsulfonium tetrafluoroborate, diphenyliodonium hexafluoroarsenate, diphenyliodonium trifluoromethanesulfonate, 2-(3, 4-dimethoxystyryl)-4,6-bis(trichloromethyl)-1,3,5-triazine, 2-[2-(furan-2-yl)vinyl]-4,6-bis(trichloromethyl)-1,3,5-triazine, 4-isopropyl-4'-methyldiphenyliodonium tetrakis(pentafluorophenyl)borate, 2-[2-(5-methylfuran-2-yl)vinyl]-4,6-bis(trichloromethyl)-1, 3,5-triazine, 2-(4-methoxyphenyl)-4,6-bis(trichloromethyl)-1, 3,5-triazine, 4-nitrobenzenediazonium tetrafluoroborate, (4-nitrophenyl)(phenyl)iodonium trifluoromethanesulfonate, triphenylsulfonium tetrafluoroborate, triphenylsulfonium bromide, tri-p-tolylsulfonium hexafluorophosphate, tri-p-tolylsulfonium trifluoromethanesulfonate, (1R,2S,5R)-5-methyl-2-(propan-2-yl)cyclohexyl 4-methylbenzenesulfonate, bis[4-n-alkyl(C 10-13)phenyl]iodonium hexafluorophosphate, cyclohexyl 4-methylbenzenesulfonate, and the like.

Alternatively, commercially available products may be used. Examples thereof include "Sunaid SI-60L, SI-100L, SI-150L" manufactured by SANSHIN CHEMICAL INDUSTRY CO., LTD., "TPS", "DBPI" manufactured by Midori Kagaku Co., Ltd., "UVI-6990" manufactured by Dow Chemical, "Irgacure 261" manufactured by Ciba-Geigy, and the like.

(ii) Examples of the latent pH adjusting agent which generates a base by heating (heat base generator) include 1,2-diisopropyl-3-[bis(dimethylamino)methylenelguadinium 2-(3-benzoylphenyl)propionate, 1,2-dicyclohexyl-4, 4,5,5-tetramethylbiguadinium n-butyltriphenylborate, (Z)-{[bis(dimethylamino)methylidene]amino)}-N-cyclohexyl (cyclohexylamino)methaniminium tetrakis(3-fluorophenyl) borate, acetophenone O-benzoyloxime, 1,2-bis(4-methoxyphenyl)-2-oxoethyl cyclohexylcarbamate, dimethyl 1, 4-dihydro-2,6-dimethyl-4-(2-nitrophenyl)-3,5-pyridinedicarboxylate, 2-nitrobenzyl cyclohexylcarbamate, 2-(9-oxoxanthen-2-yl)propionate 1,5,7-triazabicyclo[4.4.0]dec-5-ene, 2-(9-oxoxanthen-2-yl)propionic acid 1,5,7-triazabicyclo[4.4.0]dec-5-ene, and the like.

(iii) Examples of the latent pH adjusting agent which generates an acid by irradiation of energy radiation (light acid generator) include bis(cyclohexylsulfonyl)diazomethane, 2-methyl-2-[(4-methylphenyl)sulfonyl]-1-[4-(methylthio)phenyl]-1-propanone, bis(tert-butylsulfonyl)diazomethane, bis(4-methylphenylsulfonyl)diazomethane, diphenyl-4-methylphenylsulfonium trifluoromethanesulfonate, diphenyl-2,4,6-trimethylphenylsulfonium p-toluenesulfonate, diphenyl(4-methoxyphenyl)sulfonium trifluoromethanesulfonate, 4-methylphenyldiphenylsulfonium nonafluorobutanesulfonate, tris(4-methylphenyl)sulfonium nonafluorobutanesulfonate, (1R,2S,5R)-5-methyl-2-(propan-2-yl)cyclohexyl 4-methoxybenzenesulfonate, bis(4-tert-butylphenyl)iodonium hexafluorophosphate, bis(4-fluorophenyl)iodonium trifluoromethanesulfonate, cyclopropyldiphenylsulfonium tetrafluoroborate, diphenyliodonium hexafluoroarsenate, diphenyliodonium trifluoromethanesulfonate, 2-(3, 4-dimethoxystyryl)-4,6-bis(trichloromethyl)-1,3,5-triazine, 2-[2-(furan-2-yl)vinyl]-4, 6-bis(trichloromethyl)-1,3,5-triazine, 4-isopropyl-4'-methyldiphenyliodonium tetrakis(pentafluorophenyl)borate, 2-[2-(5-methylfuran-2-yl)vinyl]-4,6-bis(trichloromethyl)-1, 3,5-triazine, 2-(4-methoxyphenyl)-4,6-bis(trichloromethyl)-1, 3,5-triazine, 4-nitrobenzenediazonium tetrafluoroborate, (4-nitrophenyl)(phenyl)iodonium trifluoromethanesulfonate, triphenylsulfonium tetrafluoroborate, triphenylsulfonium bromide, tri-p-tolylsulfonium hexafluorophosphate, tri-p-tolylsulfonium trifluoromethanesulfonate, and the like.

Alternatively, commercially available products may be used. Examples thereof include "Sunaid SI-60L, SI-100L, SI-150L" manufactured by SANSHIN CHEMICAL INDUSTRY CO., LTD., "BBI-109", "TPS", "DBPI" manufactured by Midori Kagaku Co., Ltd., "UVI-6990" manufactured by Dow Chemical, "Irgacure 261" manufactured by Ciba-Geigy, and the like.

(iv) Examples of the latent pH adjusting agent which generates a base by irradiation of energy radiation (light base generator) include (Z)-{[bis(dimethylamino)methylidene]amino}-N-cyclohexyl(cyclohexylamino)methaniminium tetrakis(3-fluorophenyl)borate, 1,2-dicyclohexyl-4,4,5,5-tetramethylbiguadinium n-butyltriphenylborate, 1,2-diisopropyl-3-[bis(dimethylamino)methylene]guadinium 2-(3-benzoylphenyl)propionate, 9-anthrylmethyl N,N-diethylcarbamate, (E)-1-piperidino-3-(2-hydroxyphenyl)-2-propene-1-one, 1-(anthraquinon-2-yl)ethyl imidazolecarboxylate, 2-nitrophenylmethyl 4-methacryloyloxypiperidine-1-carboxylate, acetophenone O-benzoyloxime, 1,2-bis(4-methoxyphenyl)-2-oxoethyl cyclohexylcarbamate, dimethyl 1, 4-dihydro-2, 6-dimethyl-4-(2-nitrophenyl)-3,5-pyridinedicarboxylate, 2-nitrobenzyl cyclohexylcarbamate, 2-(9-oxoxanthen-2-yl)propionic acid, 1,5,7-triazabicyclo[4.4.0]dec-5-ene, 1,5,7-triazabicyclo[4.4.0]dec-5-ene 2-(9-oxoxanthen-2-yl)propionate, and the like.

The time of addition of the latent pH adjusting agent is not particularly limited, as far as it exists in the cavity partitioned with the outer shells at least at the time of gelling. For example, by dissolving the latent pH adjusting agent in a mixture comprising the silica precursor and the monomer at the time of suspension polymerization, it can be made to exist in the cavity. When the latent pH adjusting agent is used, a gelling temperature can be 35 to 180° C. and a gelling time can be 0.1 to 48 hours.

(3) Other Steps

Silica-including particles after the gelling step can be taken out from the emulsified liquid by passing through centrifugation, water washing, and drying, according to necessity.

(Intended Use)

Silica-including particles can be used in intended use such as cosmetic materials, paint compositions, heat-insulating resin compositions, light diffusing resin compositions, and light diffusion films.

(1) Cosmetic Material

It is preferable that the cosmetic material comprises silica-including particles in a range of 1 to 40% by weight.

Examples of the cosmetic material include cosmetics for cleansing such as soap, body shampoo, cleansing cream, and facial scrub; skin lotion, cream, milky lotion, packs, face powder, foundation, lipstick, lip cream, rouge, eye/eyebrow cosmetic, manicure cosmetic, hair washing cosmetic, hair dye, hairdressing, aromatic cosmetic, tooth paste, bath agent, antiperspirant, sunscreen product, suntan product; cosmetics for body such as body powder and baby powder; shaving cream; lotions such as pre-shaving lotion, after shaving lotion, and body lotion; and the like.

Additionally, ingredients which are generally used in cosmetic materials can be blended depending on the purpose, in a range that the effect of the present invention is not deteriorated. Examples of such ingredients include water, lower alcohols, fats or oils and waxes, hydrocarbons, higher fatty acids, higher alcohols, sterols, fatty acid esters, metal soaps, moisturizing agents, surfactants, polymer compounds, coloring material raw materials, perfumes, preservatives and antiseptics, antioxidants, ultraviolet absorbing agents, and special blending ingredients.

Examples of the fats or oils and the waxes include avocado oil, almond oil, olive oil, cacao butter, beef tallow, sesame butter, wheat germ oil, safflower oil, shea butter, turtle oil, *camellia* oil, persic oil, castor oil, grape oil, macadamia nut oil, mink oil, egg-yolk oil, Japan wax, palm oil, rosehip oil, hardened oil, silicone oil, orange roughy oil, carnauba wax, candelilla wax, whale wax, jojoba oil, montan wax, bee wax, lanolin, and the like.

Examples of the hydrocarbon include liquid paraffin, Vaseline, paraffin, ceresin, microcrystalline wax, squalene, and the like. Examples of the higher fatty acid include lauric acid, myristic acid, palmitic acid, stearic acid, oleic acid, behenic acid, undecylenic acid, oxystearic acid, linoleic acid, lanolin fatty acid, and synthetic fatty acid.

Examples of the higher alcohol include lauric alcohol, cetyl alcohol, cetostearyl alcohol, stearyl alcohol, oleyl alcohol, behenyl alcohol, lanolin alcohol, hydrogenated lanolin alcohol, hexyldecanol, octyldecanol, isostearyl alcohol, jojoba alcohol, decyltetradecanol, and the like.

Examples of the sterol include cholesterol, dihydrocholesterol, phytocholesterol, and the like.

Examples of the fatty acid ester include ethyl linoleate, isopropyl myristate, lanolin fatty acid isopropyl, hexyl laurate, myristyl myristate, cetyl myristate, octyldodecyl myristate, decyl oleate, octyldodecyl oleate, hexadecyl dimethyloctanoate, cetyl isooctanoate, decyl palmitate, trimyristic acid glycerin, tri(caprylic/capric acid) glycerin, dioleic acid propylene glycol, triisostearic acid glycerin, triisooctanoic acid glycerin, cetyl lactate, myristyl lactate, diisostearyl malate or cholesteryl isostearate, cyclic alcohol fatty acid esters such as cholesteryl 12-hydroxystearate, and the like.

Examples of the metal soap include zinc laurate, zinc myristate, magnesium myristate, zinc palmitate, zinc stearate, aluminum stearate, calcium stearate, magnesium stearate, zinc undecylenate, and the like.

Examples of the moisturizing agent include glycerin, propylene glycol, 1,3-butylene glycol, polyethylene glycol, sodium dl-pyrrolidonecarboxylate, sodium lactate, sorbitol, sodium hyaluronate, polyglycerin, xylit, maltitol, and the like.

Examples of the surfactant include anionic surfactants such as higher fatty acid soap, higher alcohol sulfuric acid ester, N-acylglutamic acid salt, and phosphoric acid ester salt; cationic surfactants such as amine salt and quaternary ammonium salt; amphoteric surfactants such as betaine type, amino acid type, imidazoline type, and lecithin; and nonionic surfactants such as fatty acid monoglyceride, propylene glycol fatty acid ester, sorbitan fatty acid ester, sucrose fatty acid ester, polyglycerin fatty acid ester, and ethylene oxide condensate.

Examples of the polymer compound include natural polymer compounds such as gum arabic, tragacanth gum, guar gum, locust bean gum, karaya gum, irismoss, quince seed, gelatin, shellac, rosin, and casein; semisynthetic polymer compounds such as carboxymethylcellulose sodium, hydroxyethylcellulose, methylcellulose, ethylcellulose, sodium alginate, ester gum, nitrocellulose, hydroxypropylcellulose, and crystalline cellulose; and synthetic polymer compounds such as polyvinyl alcohol, polyvinylpyrrolidone, polysodium acrylate, carboxyvinyl polymer, polyvinyl methyl ether, polyamide resin, silicone oil, and resin particles such as nylon particles, polymethyl methacrylate particles, crosslinked polystyrene particles, silicon particles, urethane particles, polyethylene particles, and silica particles.

Examples of the coloring material raw material include inorganic pigments such as iron oxide, ultramarine, Prussian blue, chromium oxide, chromium hydroxide, carbon black, manganese violet, titanium oxide, zinc oxide, talc, kaolin, mica, calcium carbonate, magnesium carbonate, isinglass, aluminum silicate, barium silicate, calcium silicate, magnesium silicate, silica, zeolite, barium sulfate, calcined calcium sulfate (calcined gypsum), calcium phosphate, hydroxyapatite, and ceramic powder; and tar dyes such as azo-based, nitro-based, nitroso-based, xanthene-based, quinoline-based, anthraquinoline-based, indigo-based, triphenylmethane-based, phthalocyanine-based, and pyrene-based tar dyes.

Herein, powder raw materials of the above-mentioned polymer compounds and coloring material raw materials may have been surface-treated in advance. As a surface treating method, the previously known surface treating technique can be utilized. For example, examples thereof include treating methods such as oil treatment with hydrocarbon oil, ester oil, lanolin or the like, silicone treatment with dimethylpolysiloxane, methylhydrogenpolysiloxane, methylphenylpolysiloxane or the like, fluorine compound treatment with perfluoroalkyl group-containing ester, perfluoroalkylsilane, perfluoropolyether, a polymer having a perfluoroalkyl group or the like, silane coupling agent treatment with 3-methacryloxypropyltrimethoxysilane, 3-glycidoxypropyltrimethoxysilane or the like, titanium coupling agent treatment with isopropyltriisostearoyl titanate, isopropyltris(dioctylpyrophosphate)titanate or the like, metal soap treatment, amino acid treatment with acylglutamic acid or the like, lecithin treatment with hydrogenated egg-yolk lecithin or the like, collagen treatment, polyethylene treatment, moisturizing treatment, inorganic compound treatment, and mechanochemical treatment.

Examples of the perfume include natural perfumes such as lavender oil, peppermint oil, and lime oil; and synthetic perfumes such as ethylphenyl acetate, geraniol, and p-tert-butylcyclohexyl acetate. Examples of the preservative and the antiseptic include methylparaben, ethylparaben, propylparaben, benzalkonium, benzethonium, and the like.

Examples of the antioxidant include dibutylhydroxytoluene, butylhydroxyanisole, propyl gallate, tocopherol, and the like. Examples of the ultraviolet absorbing agent include inorganic absorbing agents such as fine particle titanium oxide, fine particle zinc oxide, fine particle cerium oxide, fine particle iron oxide, and fine particle zirconium oxide; and organic absorbing agents such as benzoic acid-based, paraaminobenzoic acid-based, anthranilic acid-based, salicylic acid-based, cinnamic acid-based, benzophenone-based, and dibenzoylmethane-based absorbing agents.

Examples of the special blending ingredient include hormones such as estradiol, estrone, ethynylestradiol, cortisone, hydrocortisone, and prednisone; vitamins such as vitamin A, vitamin B, vitamin C, and vitamin E; skin astringents such as citric acid, succinic acid, lactic acid, aluminum chloride, aluminum/potassium sulfate, aluminum chlorohydroxy allantoinate, zinc paraphenol sulfonate, and zinc sulfate; hair growth promotors such as cantharis tincture, capsicum tincture, ginger tincture, Swertia japonica extract, garlic extract, hinokitiol, carpronium chloride, pentadecanoic acid glyceride, vitamin E, estrogen, and photosensitizer; and whitening agents such as phosphoric acid-L-magnesium ascorbate and kojic acid.

(2) Paints and Heat-Insulating and Light Diffusing Compositions

These compositions contain, if necessary, a binder resin, an UV curable resin, a solvent, and the like. As the binder resin, a resin which is soluble in an organic solvent or water, or an emulsion-type aqueous resin which can be dispersed in water can be used.

Addition amounts of the binder resin or the UV curable resin and silica-including particles are different depending on a thickness of a formed coated film, an average particle diameter of silica-including particles, and a coating method. An addition amount of the binder resin is preferably 5 to 50% by weight based on a total of the binder resin (solid content when the emulsion-type aqueous resin is used) and silica-including particles. The more preferable content is 10 to 50% by weight and the further preferable content is 20 to 40% by weight.

Examples of the binder resin include an acrylic resin, an alkyd resin, a polyester resin, a polyurethane resin, a chlorinated polyolefin resin, an amorphous polyolefin resin, and the like, and examples of the UV curable resin include polyfunctional (meth)acrylate resins such as polyhydric alcohol polyfunctional (meth)acrylate; polyfunctional urethane acrylate resins which are synthesized from diisocyanate, polyhydric alcohol, and (meth)acrylic acid ester having a hydroxy group; and the like.

As the UV curable resin, a polyfunctional (meth)acrylate resin is preferable, and a polyhydric alcohol polyfunctional (meth)acrylate resin having three or more (meth)acryloyl groups in one molecule is more preferable. Examples of the polyhydric alcohol polyfunctional (meth)acrylate resin having three or more (meth)acryloyl groups in one molecule include, specifically, trimethylolpropane tri(meth)acrylate, trimethylolethane tri(meth)acrylate, 1,2,4-cylohexane tetra (meth)acrylate, pentaglycerol triacrylate, pentaerythritol tetra(meth)acrylate, pentaerythritol tri(meth)acrylate, dipentaerythritol triacrylate, dipentaerythritol pentaacrylate, dipentaerythritol tetra(meth)acrylate, dipentaerythritol hexa (meth)acrylate, tripentaerythritol triacrylate, tripentaerythritol hexaacrylate, and the like, and these may be used alone, or two or more may be used concurrently.

When the UV curing resin is used, usually, a photopolymerization initiator is used concurrently. The photopolymerization initiator is not particularly limited.

Examples of the photopolymerization initiator include acetophenones, benzoins, benzophenones, phosphine oxides, ketals, α-hydroxyalkylphenones, α-aminoalkylphenones, anthraquinones, thioxanthones, azo compounds, peroxides (described in Japanese Unexamined Patent Application, First Publication No. 2001-139663 and the like), 2,3-dialkyldione compounds, disulfide compounds, fluoroamine compounds, aromatic sulfoniums, onium salts, borate salts, active halogen compounds, α-acyloxime esters, and the like.

These binder resins or UV curable resins can be appropriately selected, depending on adherability of paint to a substrate to be coated, the environment used, and the like.

The solvent is not particularly limited, but it is preferable to use a solvent which can dissolve or disperse the binder resin or the UV curable resin. For example, in the case of an oil-based paint, examples of the solvent include hydrocarbon-based solvents such as toluene and xylene; ketone-based solvents such as methyl ethyl ketone and methyl isobutyl ketone; ester-based solvents such as ethyl acetate and butyl acetate; ether-based solvents such as dioxane, ethylene glycol diethyl ether, and ethylene glycol monobutyl ether; and the like. In the case of a water-based paint, water, alcohols, and the like can be used. These solvents can be used alone or can be used by mixing two or more of them. The content of the solvent in a coating material is usually about 20 to 60% by weight based on the total amount of the composition.

The composition may contain, if necessary, a coated surface adjusting agent, a fluidity adjusting agent, an ultraviolet absorbing agent, a light stabilizer, a curing catalyst, an extender pigment, a coloring pigment, a metal pigment, a mica powder pigment, a dye, and the like, which are known.

A method of forming a coated film using the composition is not particularly limited, but any of the known methods can be used. Examples include methods such as a spray coating method, a roll coating method, and a brush coating method, and in order to coat the composition as a thin layer on a substrate such as a film, examples include a coating reverse roll coating method, a gravure coating method, a die coating method, a comma coating method, and a spray coating method. The composition may be diluted, if necessary, in order to adjust the viscosity. Examples of the diluent include hydrocarbon-based solvents such as toluene and xylene; ketone-based solvents such as methyl ethyl ketone and methyl isobutyl ketone; ester-based solvents such as ethyl acetate and butyl acetate; ether-based solvents such as dioxane and ethylene glycol diethyl ether; water; alcohol-based solvents; and the like. These diluents may be used alone or may be used by mixing two or more of them.

A coated film can be formed by coating the composition on arbitrary coating surface such as a substrate to prepare a coating film, and drying this coating film, thereafter, if necessary, curing the coating film. In addition, the coated film using a paint composition is used by coating it on various substrates, and the substrate is not particularly limited, but includes metal, timber, glass, plastic, and the like. Alternatively, the coated film can also be used by coating it on a transparent substrate such as PET, PC, and acryl.

(3) Light Diffusion Film

A light diffusion film is such that a light diffusing layer derived from the above-mentioned light diffusing composition is formed on a surface of a substrate such as glass, a plastic sheet of polycarbonate, an acrylic resin, PET, TAC or the like, a plastic film, a plastic lens, and a plastic panel, or a substrate such as a cathode ray tube, a fluorescent display tube, and a liquid crystal display plate. Although different depending on intended use, a coating film alone, or in combination with a protective film, a hard coat film, a flattening film, a high refractive index film, an insulating film, an electrically conductive resin film, an electrically conductive metal fine particle film, an electrically conductive metal oxide fine particle film, another optionally used primer film or the like, is formed on a substrate. In addition, when used in combination, a light diffusing layer is not always necessarily formed on an outermost surface.

EXAMPLES

The present invention will be illustrated more specifically below by way of Examples, but the present invention is not limited to them. First, measuring methods in Examples will be illustrated.

(Measurement of Volume Average Particle Diameter)

A volume average particle diameter of silica-including particles was measured with Coulter Multisizer™ 3 (measuring device manufactured by Beckman Coulter). Measurement was performed using apertures which had been calibrated according to Multisizer™ 3 user's manual which is issued by Beckman Coulter.

In addition, selection of apertures used in measurement was appropriately performed as follows. When a supposed volume average particle diameter of particles to be measured is 1 μm or more and 10 μm or less, an aperture having a size of 50 μm was selected, when a supposed volume average particle diameter of particles to be measured is more than 10 μm and 30 μm or less, an aperture having a size of 100 μm was selected, when a supposed volume average particle diameter of particles is more than 30 μm and 90 μm or less, an aperture having a size of 280 μm was selected, when a supposed volume average particle diameter of particles is more than 90 μm and 150 μm or less, an aperture having a size of 400 μm was selected, and so on. When a volume average particle diameter after measurement is different from a supposed volume average particle diameter, the aperture was changed to an aperture having an appropriate size and measurement was performed again.

Additionally, when an aperture having a size of 50 μm was selected, Current (aperture current) was set at −800 and Gain (gain) was set at 4, when an aperture having a size of 100 μm was selected, Current (aperture current) was set at −1600 and Gain (gain) was set at 2, and when apertures having a size of 280 μm and 400 μm were selected, Current (aperture current) was set at −3200 and Gain (gain) was set at 1.

As a measurement sample, a sample which had been obtained by dispersing 0.1 g of polymer particles in 10 ml of a 0.1% by weight aqueous nonionic surfactant solution using a touch mixer ("TOUCH MIXER MT-31" manufactured by YAMATO SCIENTIFIC CO., LTD.) and an ultrasonic cleaner ("ULTRASONICCLEANER VS-150" manufactured by Velvo-Clear) to obtain the dispersion was used. During measurement, mild stirring had been performed in a beaker in advance to a degree that air bubbles do not formulate therein, and at the time point at which 100,000 of particles were measured, measurement was terminated. A volume average particle diameter of particles was the arithmetical mean in a particle size distribution based on the volume of 100,000 particles.

(Measurement of Apparent Specific Gravity)

According to JIS Z 8807:2012, the specific gravity of particles was measured by the method below.

Concerning the specific gravity of silica-including particles, first, 10 g of particles were collected in a crucible, and dried at 100° C. for 2 hours. Then, the particles were cooled in a desiccator, 3 to 4 g of the dried particles were placed into a 25 ml pycnometer, distilled water was added to suspend them, dispersion and defoaming of the particles were performed in an ultrasound bath, and thereafter, a temperature was adjusted with a 25° C. thermostat bath. Distilled water was added up to a marked line of the pycnometer to adjust the volume, and the volume (ml) of particles was calculated from a difference between the volume (25 ml) of the pycnometer and the volume (ml) of the distilled water. From the weight (g) of added particles and the calculated volume (ml), the density was obtained.

(Measurement of Thickness of Outer Shell)

A cross section of the resulting particles was observed with a scanning electron microscope (SEM), arbitrary 30 particles having a particle diameter near a volume average particle diameter were observed, and an average thickness of the outer shell was measured.

In addition, it could be confirmed that the composition of the outer shell is constituted of a crosslinked polymer, from that little peaks derived from silica were seen on a particle surface layer by XPS (X-ray Photoelectron Spectroscopy) measurement of the resulting particles, or the like.

(Weight of Silica in Silica-Including Particles)

After 1.0 g of particles to be measured was weighed, the weighed silica-including microcapsule particles were burned up in an electric furnace at 550° C. for 30 minutes, and the weight (g) of the remaining residue was measured. Thereafter, the measured weight (g) of the residue was divided by the weight (1.0 g) of the particles before measurement to perform conversion into percentage, to obtain the ignition residue (% by weight). The resulting ignition residue (% by weight) represents the content of silica in composite resins.

(Oil Absorption Measurement)

Oil absorption of silica-including particles was measured by a method in which a purified linseed oil was used in place of a boiled linseed oil, and endpoint determination criteria were changed (an endpoint was changed to the time point at which "a measurement plate was erected and a sample began to flow"), based on the measuring method of JIS K 5101-13-2. Details of measurement of oil absorption were as follows.

(A) Device and Equipment

Measurement plate: Smooth glass plate larger than 300×400×5 mm

Palette knife (spatula): Knife with a handle having a blade made of steel or stainless Chemical balance (measuring instrument): Balance which can measure up to order of 10 mg Burette: Burette having a volume of 10 ml, defined in JIS R 3505

(B) Reagent

Purified linseed oil: Oil defined in ISO 150 (this time, extra pure linseed oil (manufactured by Wako Pure Chemical Industries, Ltd.) was used)

(C) Measuring Method (1) 1 g of silica-including particles (sample) were taken at a central part on a measurement plate, a purified linseed oil was gradually added dropwise to a center of the particles from a burette by each 4 or 5 drops per one time, and every time, the whole of the particles and the purified linseed oil were sufficiently kneaded with a palette knife.

(2) The above-mentioned dropwise addition and kneading were repeated, and when the whole of the particles and a purified linseed oil became a hard putty mass, kneading was performed for every one drop, and a point at which paste (kneading product of particles and purified linseed oil) is rapidly softened by last one drop addition of a purified linseed oil, and begins to flow was defined as an endpoint.

(3) Determination of Flow

In the case where paste was softened rapidly by dropwise addition of final one drop of a purified linseed oil and the paste moved when the measurement plate was erected vertically, it was determined that the paste is flowing. In the case where the paste did not move even when the measurement plate was erected vertically, one drop of a purified linseed oil was further added.

(4) A consumed amount of a purified linseed oil which reached an endpoint was read as decrease in a liquid amount in the burette.

(5) Measurement was performed so that the measurement time of one time is terminated within 7 to 15 minutes, and when the measurement time exceeded 15 minutes, remeasurement was performed, and a numerical value when measurement was terminated within the defined time was adopted.

(D) Calculation of Oil Absorption

Oil absorption per 100 g of silica-including particles was calculated by the formula below.

$$O = (V/m) \times 100$$

Herein, O: oil absorption (ml/100 g), m: weight of silica-including particles (g), V: volume of consumed purified linseed oil (ml).

Example 1

25 g of methyl methacrylate (MMA) as a monofunctional monomer, 25 g of ethylene glycol dimethacrylate (EGDMA) as a crosslinking monomer, 40 g of tetraethoxysilane (TEOS) as a silica precursor, 10 g of cyclohexane as a non-reactive organic solvent, and 0.5 g of 2,2'-azobis(4-methoxy-2,4-dimethylvaleronitrile) (manufactured by Wako Pure Chemical Industries, Ltd.; product name V-70) as a polymerization initiator were mixed and dissolved to prepare a mixture. The resulting mixture was mixed into 300 ml of an aqueous polyvinyl alcohol (PVA) (manufactured by The Nippon Synthetic Chemical Industry Co., Ltd.; product name Gohsenol GH-17) solution which had been prepared at the concentration of 1% by weight. The resulting mixed solution was placed into a 1 L beaker, and emulsification and dispersion treatment was performed at a rotation number of 4,000 rpm for 3 minutes using a homomixer (manufactured by PRIMIX Corporation; product name Homomixer MK-II Model 2.5).

The resulting emulsified liquid was placed into a 500 ml glass separable flask, and polymerization was performed at a temperature of 50° C. for 8 hours while stirring at 200 rpm with a turbine-like stirring impeller having a diameter of 8 cm, to obtain microcapsules including TEOS as a silica precursor in the interior thereof.

Thereafter, a one-fold equivalent of TEOS in aqueous ammonia was placed into an emulsified liquid under the condition of 30° C., and the mixture was stirred for 24 hours, thereby, silica-including particles were obtained by progression of a gelling reaction of TEOS in microcapsules.

The resulting silica-including particles were taken out from the emulsified liquid by subjecting them to centrifugation and separation of the supernatant, water washing was repeated, purification was performed, and thereafter, the particles were dried in a vacuum oven at 60° C.

The resulting silica-including particles are non-porous, a surface photograph is shown in FIG. 1 (a), and a cross-sectional photograph is shown in FIG. 1 (b). Additionally, the particles had a volume average particle diameter of 22.3 µm and the apparent specific gravity of 0.65 g/cm$^3$. Furthermore, a thickness of an outer shell in the silica-including particles was 2.3 µm and the weight of silica in the silica-including particles was 17.2% by weight.

Example 2

According to the same manner as that of Example 1 except that toluene was used in place of cyclohexane, silica-including particles were obtained.

Figure 2:
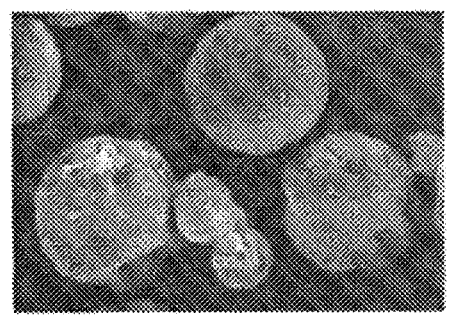
FIG. 2 is a surface photograph and a cross-sectional photograph of silica-including microcapsule resin particles of Example 2.
Figure 2:
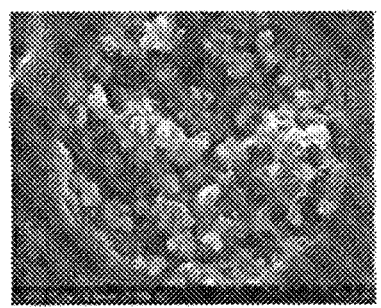

The resulting silica-including particles are non-porous, a surface photograph is shown in FIG. 2 (a), and a cross-sectional photograph is shown in FIG. 2 (b). Additionally, the particles had a volume average particle diameter of 12.5 µm and the apparent specific gravity of 0.68 g/cm$^3$. Furthermore, a thickness of an outer shell of the silica-including particles was 1.2 µm and the weight of silica in the silica-including particles was 17.5% by weight.

Example 3

According to the same manner as that of Example 1 except that 35 g of TEOS was used and 15 g of toluene was used in place of cyclohexane, silica-including particles were obtained.

Figure 3:
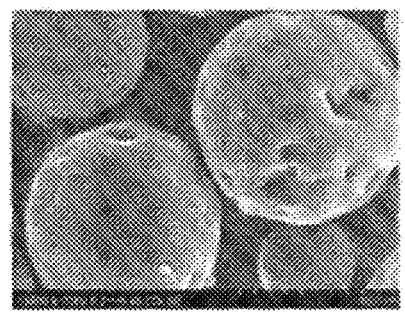
FIG. 3 is a surface photograph and a cross-sectional photograph of silica-including microcapsule resin particles of Example 3.
Figure 3:
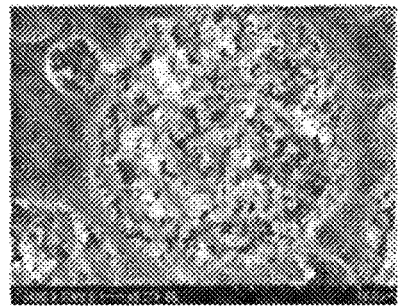

The resulting silica-including particles are non-porous, a surface photograph is shown in FIG. 3 (a), and a cross-sectional photograph is shown in FIG. 3 (b). Additionally, the particles had a volume average particle diameter of 20.5 µm and the apparent specific gravity of 0.63 g/cm$^3$. Furthermore, a thickness of an outer shell of the silica-including particles was 2.1 μm and the weight of silica in the silica-including particles was 15.8% by weight.

Example 4

According to the same manner as that of Example 1 except that 50 g of a siloxane oligomer (manufactured by Tama Chemicals Co., Ltd.; product name Silicate 45) was used in place of TEOS, cyclohexane was not used, and 1.5 g of acetoalkoxy aluminum diisopropionate (manufactured by Ajinomoto Fine-Techno Co., Ltd.; product name PLEN-ACT AL-M) was used as an aluminum-based alkoxide compound, silica-including particles were obtained.

Figure 4:
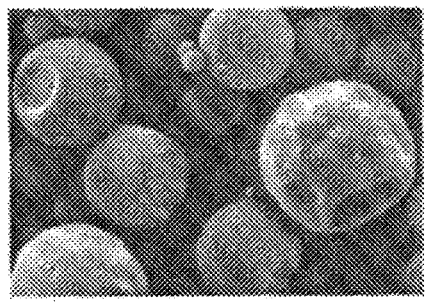
FIG. 4 is a surface photograph and a cross-sectional photograph of silica-including microcapsule resin particles of Example 4.
Figure 4:
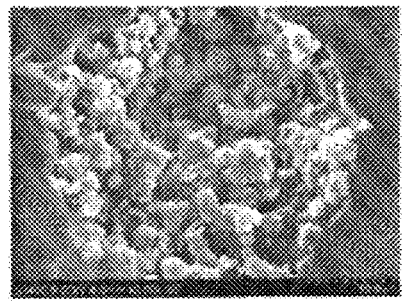

The resulting silica-including particles are non-porous, a surface photograph is shown in FIG. 4 (*a*), and a cross-sectional photograph is shown in FIG. 4 (*b*). Additionally, the particles had a volume average particle diameter of 53.5 μm and the apparent specific gravity of 0.73 g/cm³. Furthermore, a thickness of an outer shell of the silica-including particles was 4.8 μm and the weight of silica in the silica-including particles was 28.2% by weight.

Example 5

According to the same manner as that of Example 1 except that 90 g of TEOS was used and toluene was used in place of cyclohexane, silica-including particles were obtained.

The resulting silica-including particles were non-porous. Additionally, the particles had a volume average particle diameter of 14.2 μm and the apparent specific gravity of 0.58 g/cm³. Furthermore, a thickness of an outer shell of the silica-including particles was 0.8 μm and the weight of silica in the silica-including particles was 30.3% by weight.

Example 6

According to the same manner as that of Example 1 except that 20 g of TEOS was used and 5 g of toluene was used in place of cyclohexane, silica-including particles were obtained.

The resulting silica-including particles were non-porous. Additionally, the particles had a volume average particle diameter of 13.5 μm and the apparent specific gravity of 0.835 g/cm³. Furthermore, a thickness of an outer shell of the silica-including particles was 1.8 μm and the weight of silica in the silica-including particles was 8.9% by weight.

Example 7

According to the same manner as that of Example 1 except that 35 g of MMA and 15 g of EGDMA were used, and toluene was used in place of cyclohexane, silica-including particles were obtained.

The resulting silica-including particles were non-porous. Additionally, the particles had a volume average particle diameter of 10.8 μm and the apparent specific gravity of 0.67 g/cm³. Furthermore, a thickness of an outer shell of the silica-including particles was 1.1 μm and the weight of silica in the silica-including particles was 17.9% by weight.

Example 8

According to the same manner as that of Example 1 except that 15 g of TEOS was used and 35 g of toluene was used in place of cyclohexane, silica-including particles were obtained.

Figure 5:
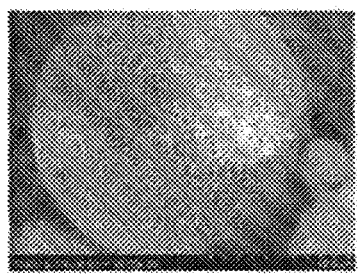
FIG. 5 is a surface photograph and a cross-sectional photograph of silica-including microcapsule resin particles of Example 8.
Figure 5:
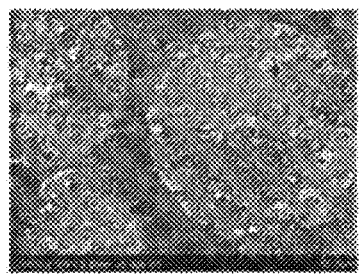

The resulting silica-including particles were porous, a surface photograph is shown in FIG. 5 (*a*), and a cross-sectional photograph is shown in FIG. 5 (*b*). Additionally, the particles had a volume average particle diameter of 11.8 μm. Furthermore, a thickness of an outer shell of the silica-including particles was 1.1 μm, the weight of silica in the silica-including particles was 10.8% by weight, and oil absorption was 220 ml/100 g.

Example 9

According to the same manner as that of Example 1 except that 25 g of TEOS was used and 25 g of toluene was used in place of cyclohexane, silica-including particles were obtained.

Figure 6:
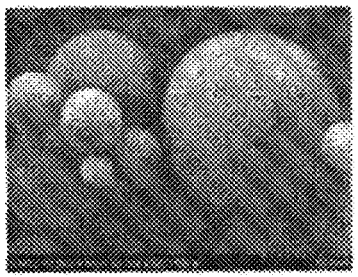
FIG. 6 is a surface photograph and a cross-sectional photograph of silica-including microcapsule resin particles of Example 9.
Figure 6:
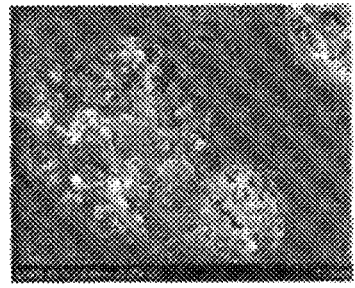

The resulting silica-including particles are porous, a surface photograph is shown in FIG. 6 (*a*), and a cross-sectional photograph is shown in FIG. 6 (*b*). Additionally, the particles had a volume average particle diameter of 15.7 μm. Furthermore, a thickness of an outer shell of the silica-including particles was 1.6 μm, the weight of silica in the silica-including particles was 11.0% by weight, and oil absorption was 350 ml/100 g.

Example 10

According to the same manner as that of Example 1 except that 35 g of TEOS was used and 15 g of ethyl acetate was used in place of cyclohexane, silica-including particles were obtained.

The resulting silica-including particles were porous. Additionally, the particles had a volume average particle diameter of 14.8 μm. Furthermore, a thickness of an outer shell of the silica-including particles was 1.5 μm, the weight of silica in the silica-including particles was 15.8% by weight, and oil absorption was 380 ml/100 g.

Example 11

According to the same manner as that of Example 1 except that 25 g of TEOS was used and 25 g of ethyl acetate was used in place of cyclohexane, silica-including particles were obtained.

The resulting silica-including particles were porous. Additionally, the particles had a volume average particle diameter of 11 μm. Furthermore, a thickness of an outer shell of the silica-including particles was 1 μm, the weight of silica in the silica-including particles was 11.2% by weight, and oil absorption was 340 ml/100 g.

(Assessment of Reflection Properties of Ultraviolet, Visible, and Near Infrared Light)

Reflectivity of silica-including microcapsule resin particles to ultraviolet light, visible light, and near infrared light was assessed by the procedure below.

Using an ultraviolet, visible, and near infrared spectrophotometer (Solid Spec 3700) manufactured by Shimadzu Corporation as a device for measuring reflectivity, and using a 60 mm integrating sphere, particles were filled into a holder for a powder sample, and thereby, a sample was obtained. Ultraviolet light to near infrared light (wavelength 200 to 2,100 nm) reflection properties of the resulting sample were measured as reflectivity (% R). An integrating sphere inner surface was coated with barium sulfate and reflectivity of the particles based on reflectivity of a BaSO₄ white plate as 100% was measured.

In addition, the above-mentioned measurement was performed on silica-including microcapsule resin particles of Example 2, and commercially available porous resin particles (manufactured by SEKISUI PLASTICS CO., LTD.; product name TECHPOLYMER MBP-8) and true spherical resin particles (manufactured by SEKISUI PLASTICS CO., LTD.; product name TECHPOLYMER MBX-8). The resulting results are shown in FIG. 7.

Figure 7:
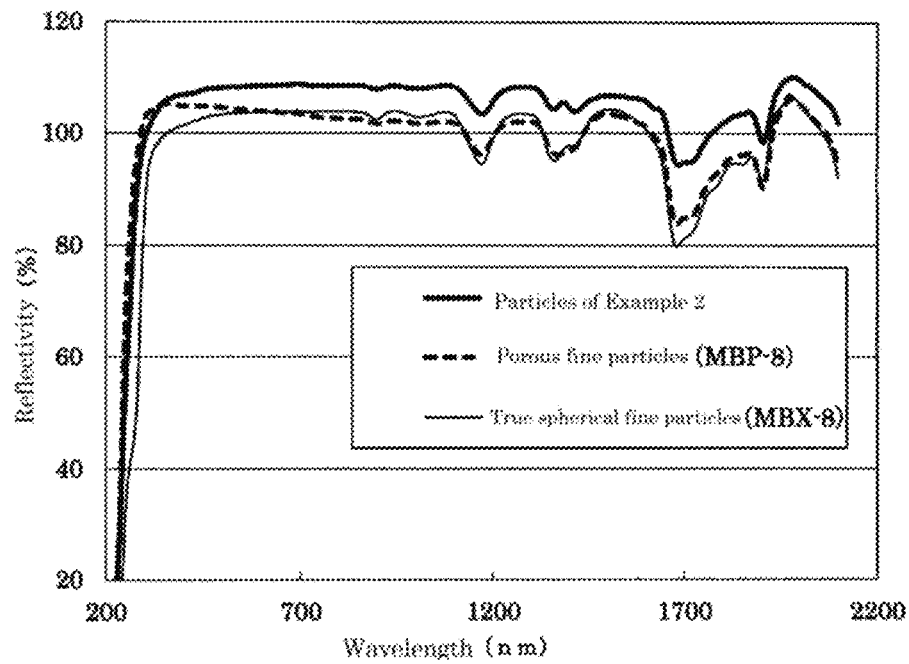
FIG. 7 is a graph showing light reflectivity for each wavelength of various particles in assessment of ultraviolet, visible, and near infrared light reflection properties.

From FIG. 7, it is seen that the silica-including microcapsule resin particles of Example 2 have high reflectivity at almost all wavelengths from ultraviolet light to near infrared light.

(Example of Heat-Insulating Property Assessment)

To 10 g of a commercially available water-based paint (manufactured by WASHIN PAINT CO., LTD.; product name Aqueous Urethane Varnish; indoor wooden part type; transparent clear) were added each 2.5 g of the silica-including microcapsule resin particles of Examples 2 and 3, and commercially available resin particles (manufactured by SEKISUI PLASTICS CO., LTD.; product name TECH-POLYMER MBX-8, MBP-8) as a comparison object, the mixture was stirred well to disperse the resin particles, and thereby, a paint for assessment was prepared.

The paint for assessment was coated on a PET plate having a thickness of 2 mm with an applicator set at a wet thickness of 500 μm, and thereafter, the coated plate was sufficiently dried in an oven set at 50° C. to prepare a sample plate for assessing heat insulating property.

The sample plate was placed on a stand at an atmospheric temperature of 23° C., with a sample-attached surface upward, an infrared lamp (Mini-ref reflection bulb 30 W, manufactured by Toshiba Lighting & Technology Corporation) was placed at a position 3 cm from below, and thereafter, a container having a volume of 150 cc was made to cover over the sample plate. A thermometer was placed at a position 5 cm above the sample plate in the container, light from an infrared lamp was irradiated for 5 minutes, and a temperature was measured. Results are shown in Table 1.

TABLE 1

| | Silica-including particles of Example 2 | Silica-including particles of Example 3 | Commercially available true spherical particles (MBX-8) | Commercially available porous particles (MBP-8) |
|---|---|---|---|---|
| Temperature in container after 5 minutes from lamp irradiation | 44.4° C. | 41.5° C. | 56.1° C. | 54.8° C. |

From the above-mentioned Table 1, it could be confirmed that in the silica-including particles of Examples 2 and 3, temperature rise is suppressed, and the particles have heat-insulating performance.

Example 12

25 g of MMA, 25 g of EGDMA, 40 g of TEOS, 10 g of toluene, 0.5 g of 2,2'-azobis(4-methoxy-2,4-dimethylvaleronitrile), and 1 g (2.5 parts by weight based on 100 parts by weight of TEOS) of (1R,2S,5R)-5-methyl-2-(propan-2-yl) cyclohexyl 4-methylbenzenesulfonate (manufactured by Wako Pure Chemical Industries, Ltd.; product name WPAG-699) as a heat acid generator were mixed and dissolved to prepare a mixture.

The resulting mixture was mixed into 300 ml of an aqueous polyvinyl alcohol (PVA) (manufactured by The Nippon Synthetic Chemical Industry Co., Ltd.; product name Gohsenol GH-17) solution which had been adjusted at the concentration of 1% by weight. The resulting mixed solution was placed into a 1 L beaker, and emulsification and dispersion treatment was performed at a rotation number of 4,000 rpm for 3 minutes using a homomixer (manufactured by PRIMIX Corporation; product name Homomixer MK-II Model 2.5).

The resulting emulsified liquid was placed into a 500 ml pressure container with an impeller, and polymerization was performed at a temperature of 50° C. for 8 hours while stirring with the impeller at 200 rpm, to obtain microcapsules containing TEOS as a silica precursor in the interior thereof.

Thereafter, by stirring the emulsified liquid at 110° C. for 2 hours, silica-including particles were obtained by progression of a gelling reaction of TEOS in microcapsules.

The resulting silica-including particles were taken out from the emulsified liquid by subjecting them to centrifugation and separation of the supernatant, water washing was repeated, purification was performed, and thereafter, the particles were dried in a vacuum oven at 60° C.

Figure 8:
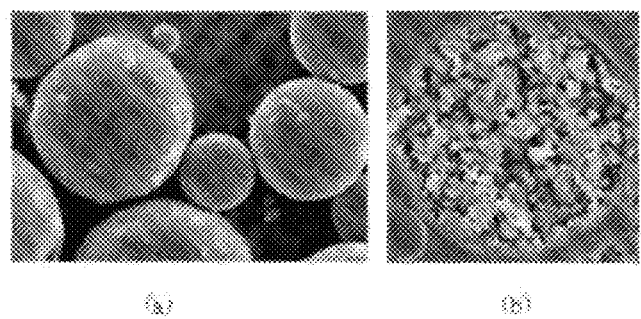
FIG. 8 is a surface photograph and a cross-sectional photograph of silica-including microcapsule resin particles of Example 12.

The resulting silica-including particles are non-porous, a surface photograph is shown in FIG. 8 (a), and a cross-sectional photograph is shown in FIG. 8 (b). Additionally, the particles had a volume average particle diameter of 11.7 μm and the apparent specific gravity of 0.6 g/cm³. Furthermore, a thickness of an outer shell of the silica-including particles was 1.1 μm and the weight of silica in the silica-including particles was 16.1% by weight.

When heat-insulating property was assessed as described above, a temperature in the container after 5 minutes from lamp irradiation was 45.4° C. and temperature rise was suppressed.

Example 13

According to the same manner as that of Example 12 except that 35 g of TEOS was used, an amount of toluene was 15 g, and an amount of (1R,2S,5R)-5-methyl-2-(propan-2-yl)cyclohexyl 4-methylbenzenesulfonate was 0.875 g, silica-including particles were obtained.

Figure 9:
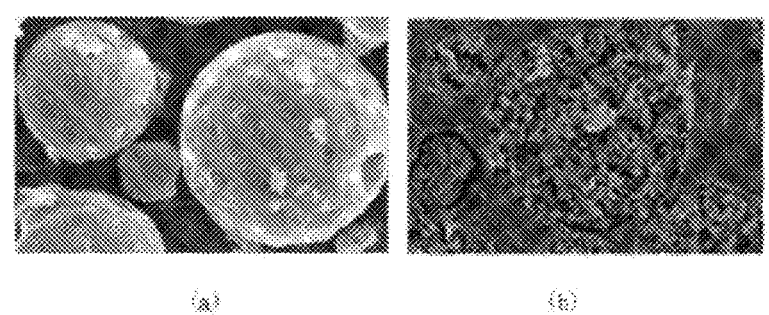
FIG. 9 is a surface photograph and a cross-sectional photograph of silica-including microcapsule resin particles of Example 13.

The resulting silica-including particles are non-porous, a surface photograph is shown in FIG. 9 (a), and a cross-sectional photograph is shown in FIG. 9 (b). Additionally, the particles had a volume average particle diameter of 19.6 μm and the apparent specific gravity of 0.59 g/cm³. Furthermore, a thickness of an outer shell of the silica-including particles was 1.9 μm and the weight of silica in the silica-including particles was 14.9% by weight.

When heat-insulating property was assessed as described above, a temperature in the container after 5 minutes from lamp irradiation was 45.2° C. and temperature rise was suppressed.

(Paint Composition Production Example 1)

2 parts by weight of the silica-including microcapsule resin particles obtained in Example 1 and 20 parts by weight of a commercially available acrylic-based aqueous glossy paint (manufactured by Kanpe Hapio Co., Ltd., product name Super Hit) were mixed for 3 minutes and defoamed for 1 minute using a stirring defoaming apparatus, and thereby, a paint composition was obtained.

The resulting paint composition was coated on an ABS resin (acrylonitrile-butadiene-styrene resin) plate using a coating device set with a blade having clearance of 75 μm, and thereafter, dried to obtain a coated film.

(Light Diffusing Resin Composition and Light Diffusion Film Production Example 1)

7.5 parts by weight of the silica-including microcapsule resin particles obtained in Example 1, 30 parts by weight of an acrylic resin (manufactured by DIC CORPORATION, product name ACRYDIC A811), 10 parts by weight of a crosslinking agent (manufactured by DIC CORPORATION, product name VM-D), and 50 parts by weight of butyl acetate as a solvent were mixed for 3 minutes and defoamed for 1 minute using a stirring defoaming apparatus, and thereby, a light diffusing resin composition was obtained.

The resulting light diffusing resin composition was coated on a PET film having a thickness of 125 µm using a coating device set with a blade having clearance of 50 µm, and dried at 70° C. for 10 minutes, and thereby, a light diffusion film was obtained.

(Formulation Example of Cosmetic Material)
(Blending Example 1)
Production of Powder Foundation
Blending Amount

| | |
|---|---|
| Silica-including microcapsule resin particles obtained in Example 1 | 10.0 parts by weight |
| Red iron oxide | 3.0 parts by weight |
| Yellow iron oxide | 2.5 parts by weight |
| Black iron oxide | 0.5 parts by weight |
| Titanium oxide | 10.0 parts by weight |
| Mica | 20.0 parts by weight |
| Talc | 44.0 parts by weight |
| Liquid paraffin | 5.0 parts by weight |
| Octyldodecyl myristate | 2.5 parts by weight |
| Vaseline | 2.5 parts by weight |
| Antiseptic | q.s. |
| Perfume | q.s. |

Production Method

Silica-including microcapsule resin particles, red iron oxide, yellow iron oxide, black iron oxide, titanium oxide, mica, and talc are mixed with a Henschel mixer, a mixture obtained by mixing and dissolving liquid paraffin, octyldodecyl myristate, vaseline, and antiseptic is added thereto, and the materials are uniformly mixed. A perfume is added thereto, and the materials are mixed, ground, and passed through a sieve. This is compression-molded into a metal tray to obtain powder foundation.

(Blending Example 2)
Production of Cosmetic Milky Lotion
Blending Amount

| | |
|---|---|
| Silica-including microcapsule resin particles obtained in Example 1 | 10.0 parts by weight |
| Stearic acid | 2.5 parts by weight |
| Cetyl alcohol | 1.5 parts by weight |
| Vaseline | 5.0 parts by weight |
| Liquid paraffin | 10.0 parts by weight |
| Polyethylene (10 mole) monooleic acid ester | 2.0 parts by weight |
| Polyethylene glycol 1500 | 3.0 parts by weight |
| Triethanolamine | 1.0 part by weight |
| Purified water | 64.5 parts by weight |
| Perfume | 0.5 parts by weight |
| Antiseptic | q.s. |

Production Method

First, stearic acid, cetyl alcohol, vaseline, liquid paraffin, and polyethylene monooleic acid ester are heated and dissolved, silica-including particles are added thereto, the materials are mixed, and the mixture is kept warm at 70° C. (oily phase). Additionally, polyethylene glycol and triethanolamine are added to purified water, the materials are heated and dissolved, and the solution is kept warm at 70° C. (aqueous phase). The oily phase is added to the aqueous phase, pre-emulsification is performed, thereafter, uniform emulsification is performed with a homomixer, and after emulsification, the emulsion is cooled to 30° C. while agitating, and thereby, cosmetic milky lotion is obtained.

What is claimed is:

1. Silica-including microcapsule resin particles, each silica- including microcapsule resin particle consisting essentially of:
   an outer shell constituted of a crosslinked polymer, the crosslinked polymer being a copolymer of a monofunctional monomer having one vinyl group and a crosslinking monomer having two or more vinyl groups;
   a cavity partitioned with said outer shell; and
   silica particles mutually connected to form a porous structure inside said cavity;
   wherein the silica-including microcapsule resin particles have a volume average particle diameter of 0.5 to 100 µm.

2. The silica-including microcapsule resin particles according to claim 1, wherein said porous structure has a weight that is 5 to 50% of a total weight of said silica-including microcapsule resin particles, and gives a hollow structure to said cavity.

3. The silica-including microcapsule resin particles according to claim 1, wherein said outer shell is porous.

4. The silica-including microcapsule resin particles according to claim 1, wherein said outer shell is porous, and said silica-including microcapsule resin particles have an oil absorption of 150 to 500 ml/100 g.

5. The silica-including microcapsule resin particles according to claim 1, wherein said outer shell is non-porous, and said silica-including microcapsule resin particles have an apparent specific gravity of 0.3 to 1.0 g/cm$^3$.

6. A method for producing the silica-including microcapsule resin particles as defined in claim 1, the method comprising the steps of:
   suspension polymerizing a mixture containing 100 parts by weight of a radical polymerizable monofunctional monomer having one vinyl group, 20 to 80 parts by weight of a crosslinking monomer having two or more vinyl groups, and 60 to 200 parts by weight of silicone alkoxide as a silica precursor in presence of a radical polymerization initiator in an aqueous medium to form an outer shell constituted of a crosslinked polymer and a cavity partitioned with said outer shell; and
   gelling silicone alkoxide after formation of said outer shell or together with formation of said outer shell to form inside said cavity a porous structure in which silica particles are mutually connected.

7. The method for producing the silica-including microcapsule resin particles according to claim 6, wherein said silicone alkoxide is a mixture including a monomer and an oligomer.

8. The method for producing the silica-including microcapsule resin particles according to claim 6, wherein said suspension polymerization is performed in absence of a non-reactive organic solvent and in presence of an alkoxide compound of titanium, zirconium or aluminum.

9. The method for producing the silica-including microcapsule resin particles according to claim 6, wherein said gellation is performed with a catalyst of an acid or a base in said cavity partitioned with said outer shell, said acid or said base is generated by external stimulation of energy radiation or heat to a latent pH adjusting agent, and said latent pH adjusting agent exists in said cavity by dissolving said latent pH adjusting agent in the mixture during the suspension polymerization.

10. A cosmetic material comprising the silica-including microcapsule resin particles as defined in claim 1.

11. A paint composition comprising the silica-including microcapsule resin particles as defined in claim 1.

12. A heat-insulating resin composition comprising the silica-including microcapsule resin particles as defined in claim 1.

13. A light diffusing resin composition comprising the silica-including microcapsule resin particles as defined in claim 1.

14. A light diffusion film comprising the silica-including microcapsule resin particles as defined in claim 1.

* * * * *